United States Patent [19]

Parks

[11] Patent Number: Plant 6,520

[45] Date of Patent: Jan. 10, 1989

[54] *PRNUS SERRULATA* (ROYAL BURGUNDY)

[76] Inventor: Franklin D. Parks, Rte. 2, Box 778, Beaverton, Oreg. 97007

[21] Appl. No.: 939,167

[22] Filed: Dec. 8, 1986

[51] Int. Cl.[4] ..... A01H 5/00

[52] U.S. Cl. ..... Plt./37

[58] Field of Search ..... Plt./37

*Primary Examiner*—Robert E. Bagwill

[57] ABSTRACT

A new variety of *Prunus serrulata* having distinctive purplish red leaf color with the blossoms being a darker purplish red than the known varieties of the *Prunus serrulata* species. The branches, stems and calyxes are reddish.

2 Drawing Sheets

1

The present invention relates to a new and distinct variety of flowering cherry tree of the species known as *Prunus serrulata.* The variety was discovered by me in a row of *Prunus serrulata* seedlings of the Kwanzan variety which by nature have medium green leaves and branches. The present new variety has been designated by me as "Royal Burgundy. "

A seedling of the Kwanzan variety was observed in a cultivated area of my nursery located in Washington County, Oreg., as having one branch the leaves of which were a shade of purplish red in contrast to the remaining leaves of the seedling and the leaves of the other seedlings. Additionally, the bark of the observed seedling branch was a dark shade of purple.

The above noted observed branch was grafted during dormancy to a mazzard seedling understock. Initial asexual propagation was achieved by such dormant grafting under my close supervision. Further asexual propagation was achieved by dormant grafting under my close supervision using mazzard seedlings as understock. Later asexual propagation has been achieved by budding and by grafting cuttings from the asexually propagated trees. Cuttings from the asexually propagated trees have been rooted in a greenhouse environment with controlled water flow and periodic misting of the leaves.

Figure 1:
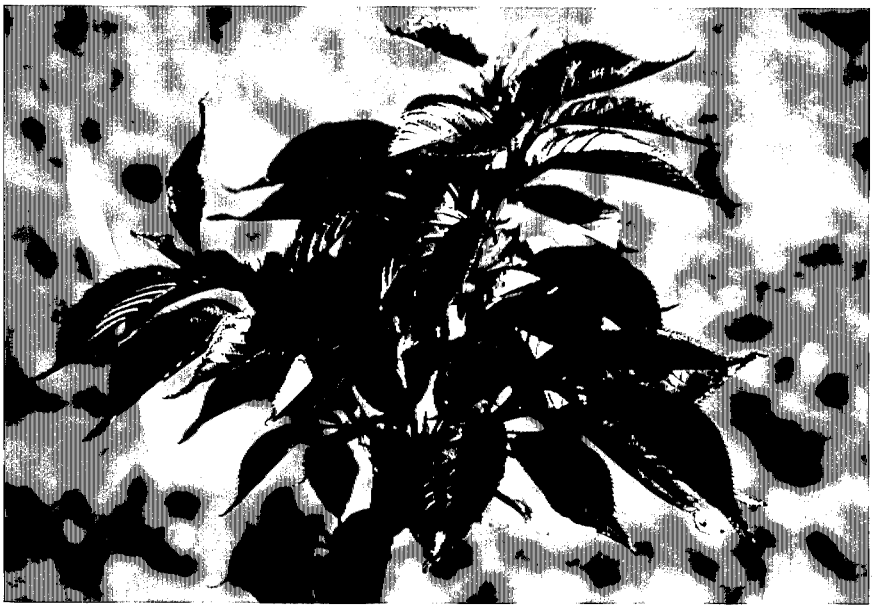
FIG. 1 is a view of a mature branch and foliage of the new variety.
Figure 2:
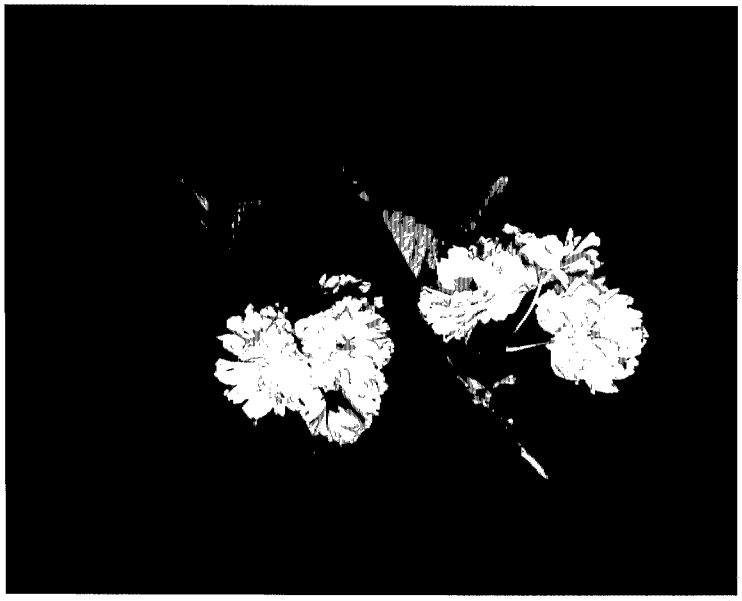
FIG. 2 is a perspective view for comparison purposes of a cutting of the new variety on the left hand side and a cutting of the Kwanzan variety on the right hand side.
Figure 3:
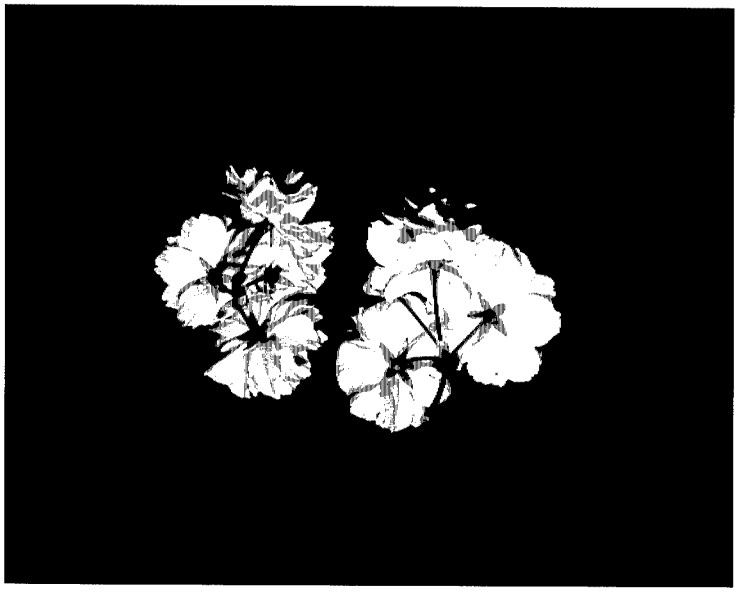
FIG. 3 is a view similar to FIG. 2 but providing a comparison between the blossoms of the new variety on the left hand side and blossoms of the Kwanzan variety on the right hand side.
Figure 4:
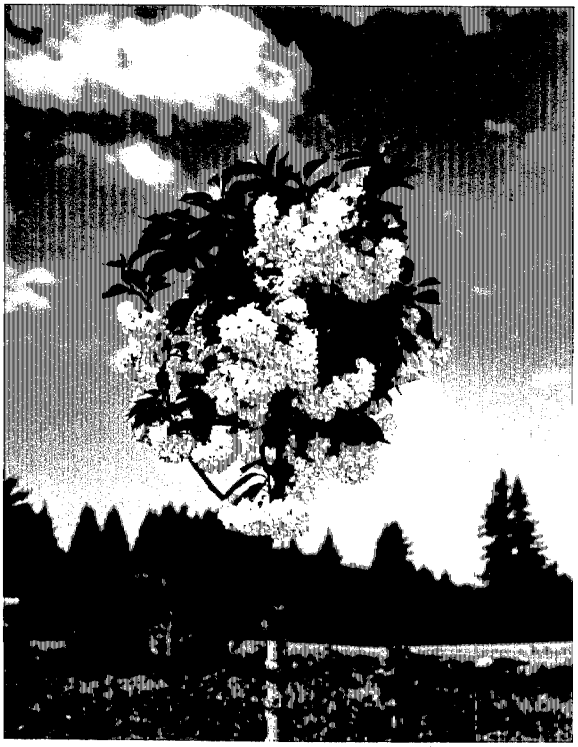
FIG. 4 is a view of the new variety of *Prunus serrulata.*

The new asexually propagated trees are distinguished from any known varieties of *Prunus serrulata* of which I am aware by reason of:

1. The flowers of the present tree are of a darker shade than those of other *Prunus serrulata* varieties;

2

2. The flower stems and calyxes are purplish red;
3. The bark is a dark shade of purple;
4. The leaves and particularly the upper surface thereof are a purplish red; and
5. At maturity in early summer the leaves and specifically the upper surfaces thereof have a glossy appearance.

The present variety of *Prunus serrulata* has been asexually reproduced in my nursery by budding, grafting and rooting with the resulting trees having a markedly different color than known varieties of the *Prunus serrulata* with color differences being in the flower, the leaf, the stem and calyx and the bark of the branches.

The following description of my new variety of *Prunus serrulata* is with reference to the Munsell Book of Color, 1976 Edition.

The size and shape of the leaves, the trunk and the branches appear to be similar to those of the Kwanzan variety of the *Prunus serrulata.*

The new variety is described as follows:

Parentage: A bud sport of a *Prunus serrulata* seedling.
Propagation: Budding and Grafting to understock. Rooting of cuttings in a greenhouse environment.
Locality: Washington County, Oreg.
Foliage:

*Leaves.*—Shape — Elliptic. Base — Cuneate. Apex — Accuminate. Margin — Serrulate. Color — purplish Red 2.5R 2/6 to 2/2. Size — Length — 8.9 cm to 10 cm. Width — 5.08 cm to 6.35 cm. Petiole — 2 cm to 2.5 cm.

*Branches.*—Color — Red 5.0 R 3/4 to 3/6.

*Stem and calyx.*—Color — purplish Red 2.5R 3/6 to 3/8.

*Blossom.*—Color — purplish Red 2.5R 8/6 to 7/8. Size — approximately 3.5 cm in diameter.

I claim:

1. A new and distinct variety of *Prunus serrulata* as described and illustrated, distinguished from the species and other known varieties by the purplish red color of its leaves, the red branches, the purplish red stem and caps and the purplish Red blossoms.

* * * * *